United States Patent [19]
Yagii et al.

[11] Patent Number: 5,914,428
[45] Date of Patent: Jun. 22, 1999

[54] PROCESS FOR PREPARATION OF ISOCYANATE COMPOUNDS

[75] Inventors: Toyokazu Yagii; Teruo Itokazu; Kenji Oka, all of Hiroshima; Yasutaka Tanaka; Hidetaka Kojima, both of Hyogo; Kiyokazu Murata, Hiroshima, all of Japan

[73] Assignee: Daicel Chemical Industries, Ltd., Osaka, Japan

[21] Appl. No.: 08/560,517

[22] Filed: Nov. 16, 1995

Related U.S. Application Data

[63] Continuation of application No. 08/218,459, Mar. 28, 1994, abandoned, which is a continuation of application No. 07/750,509, Aug. 27, 1991, abandoned, which is a continuation-in-part of application No. 07/453,954, Dec. 20, 1989, abandoned, which is a continuation-in-part of application No. 07/261,832, Sep. 9, 1988, abandoned.

[30] Foreign Application Priority Data

| Jan. 13, 1987 | [JP] | Japan | 62-4085 |
| Jun. 18, 1987 | [JP] | Japan | 62-153032 |
| Nov. 11, 1987 | [JP] | Japan | 62-284442 |
| Dec. 16, 1987 | [JP] | Japan | 63-316180 |
| Jan. 13, 1988 | [WO] | WIPO | PCT/JP86/00026 |
| Jan. 13, 1989 | [JP] | Japan | 1-7252 |
| Jun. 1, 1989 | [JP] | Japan | 1-139505 |

[51] Int. Cl.$^6$ ............... C07C 263/00; C07C 261/00
[52] U.S. Cl. ............... 560/345; 560/24; 560/157; 560/158
[58] Field of Search ............... 560/24, 157, 158, 560/345

[56] References Cited

U.S. PATENT DOCUMENTS

| 3,919,279 | 11/1975 | Rosenthal et al. | 560/345 |
| 4,081,472 | 3/1978 | Tsumura et al. | 560/345 |
| 4,330,479 | 5/1982 | Merger et al. | 560/345 |
| 4,395,565 | 7/1983 | Romano et al. | 560/24 |

*Primary Examiner*—Alan Siegel
*Attorney, Agent, or Firm*—McAulay Nissen Goldberg Kiel & Hand, LLP

[57] ABSTRACT

An aliphatic diisocyanate compound is prepared in a high yield by reacting dimethyl carbonate with an aliphatic diamine in the presence of an alkali catalyst to produce a corresponding urethane compound; and, within 48 hours after the completion of the preparation of the urethane compound, thermally decomposing the urethane compound under a reduced pressure of 1 to 700 Torr in a high-boiling-point solvent.

34 Claims, 3 Drawing Sheets

PROCESS FOR PREPARATION OF ISOCYANATE COMPOUNDS

CROSS-REFERENCE TO RELATED APPLICATION

This is a continuation, of application Ser. No. 08/218,459 filed Mar. 28, 1994, which, is a continuation of Ser. No. 07/750,509 filed Aug. 27, 1991, which, in turn, is a continuation-in-part of Ser. No. 07/453,954 filed Dec. 20, 1989, which, in turn, is a continuation-in-part of Ser. No. 07/261,832 filed Sep. 9, 1988, all now abandoned.

BACKGROUND OF THE INVENTION

1. Field of the Invention

The present invention relates to a process for the preparation of isocyanate compounds which comprises a two-stage reaction using a diamine and dimethyl carbonate as the starting materials.

2. Description of the Related Art

An isocyanate compound is an industrially valuable compound, and especially, a bifunctional isocyanate is valuable as the starting material of a polyurethane.

Currently, an isocyanate compound is industrially prepared by reaction between an amine compound and phosgene. As is well-known, phosgene is a reactive compound having a high selectivity, but phosgene has a strong toxicity, and a strict control is necessary when handling this compound. So long as the preparation using phosgene is continued, the risks of damage caused by a leakage of phosgene cannot be avoided.

As the means for preparing an isocyanate compound from an amine compound without using phosgene, there has been proposed a process in which an amine compound is reacted with urea and an alcohol to form a urethane compound and the urethane compound is thermally decomposed in the gas phase (Japanese Unexamined Patent Publication No. 59-205,352 and Japanese Unexamined Patent Publication No. 59-205,353). According to the example of this process, the first step is conducted under a pressure of 6 to 8 bars and the second step is conducted at a reaction temperature of 410° C. in the gas phase, and therefore, the equipment cost of this process is high.

A process can be considered in which dimethyl carbonate is used instead of urea and the alcohol. Compared with phosgene, dimethyl carbonate is a safe compound and a special toxicity-removing equipment or inspection is not necessary. Moreover, dimethyl carbonate is prepared from cheap compounds, that is, methanol and carbon monoxide (see, for example, Japanese Patent Application No. 61-210,568, Japanese Patent Application No. 61-215,178 and Japanese Patent Application No. 61-215,179).

Accordingly, if an isocyanate compound can be obtained by reacting an amine with dimethyl carbonate to form a urethane compound (first step) and thermally decomposing the urethane compound (second step), an economically advantageous process that can take the place of the phosgene process will be provided.

This reaction is expressed by the following reaction formulae:

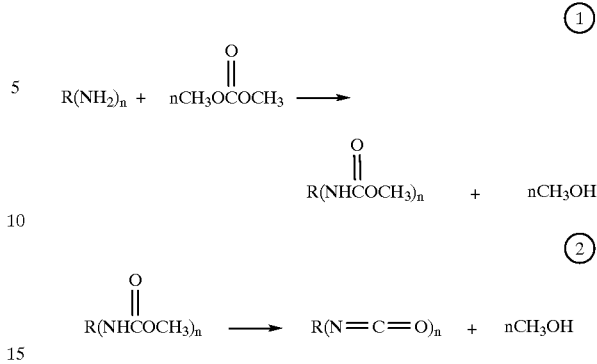

Several processes have been proposed in connection with the first step.

The speed of the reaction between a dialkyl carbonate and an amine compound is very low at a mild temperature under a mild pressure, and a catalyst is necessary to make the process practically utilizable.

The process usually a Lewis acid as the catalyst is disclosed in Japanese Examined Patent Publication No. 51-33,095. In the examples of this patent publication, aromatic amines and aliphatic amines are disclosed, but, since the amounts of the catalysts used are large and expensive uranium and antimony are used as the catalysts, the process is not advantageous from the economical viewpoint.

There has been proposed a process in which a urethane compound is prepared by reacting a carbonic acid ester with an amine compound in the presence of a base catalyst (Japanese Unexamined Patent Publication No. 54-163,527). Only examples using aniline which is an aromatic amine are disclosed in this patent publication. In this process, N-methylation as the side reaction is preferential to the urethane-forming reaction, and therefore, the yield of the intended urethane is low.

Another process has been proposed in connection with the reaction to be carried out in the presence of a base catalyst (U.S. Pat. No. 4,395,565). Two examples using aniline which is an aromatic amine are disclosed as the example using dimethyl carbonate in this patent publication.

In one of these examples, the reaction is carried out at a temperature (120° C.) higher than the boiling point (9° C.) of dimethyl carbonate under an increased pressure in an autoclave, but the conversion after 5 hours is only 40% and the methylation product is formed in an amount that cannot be neglected.

In another example, 18.5 g (0.199 mole) of aniline, 22 g (0.244 mole) of dimethyl carbonate, 1.24 g of sodium methylate and 25 ml (17.4 g) of methanol, the total amount being 61.4 g (the concentrations of the components other than methanol are 3.2 moles/kg, 4.0 moles/kg and 2.0% by weight, respectively) are reacted at 70° C. under atmospheric pressure for 5 hours. The conversion of aniline is only 15.3% and the space time yield is not satisfactory.

In this patent, it is taught that a temperature range of 100 to 140° C. is especially preferred.

In the conventional processes using a base catalyst, dimethyl carbonate is reacted with an amine only in a low yield or space time yield.

Also in connection with the reaction of the second step, several processes have been proposed. For example, Japanese Unexamined Patent Publication No. 59-205,352 and Japanese Unexamined Patent Publication No. 59-2057353 (U.S. Pat. No. 4,596,679) propose a process in which decomposition is carried out at a reaction temperature higher than 400° C. But the equipment cost is high because the reaction is preformed in the gas phase, and thus the process is economically disadvantageous.

As the process in which the reaction is carried out in the liquid phase, for example, Japanese Examined Patent Publication No. 57-45,736 (U.S. Pat. No. 4,081,472) and Japanese Unexamined Patent Publication No. 51-19,721 (U.S. Pat. No. 3,919,279) propose a process in which an isocyanate compound is obtained by thermally decomposing a urethane compound in a high-boiling-point solvent by using a metal or metal salt catalyst. But the catalyst used is a metal or metal salt free of manganese, molybdenum or tungsten and the amount of the catalyst used is relatively large, and since a method in which the catalyst is charged in the high-boiling-point solvent simultaneously with the urethane compound is adopted as the method for adding the catalyst, the reaction efficiency is still low.

Although Japanese Unexamined Patent Publication No. 51-19,721 (U.S. Pat. No. 3,919, 279) discloses a process in which thermal decomposition is carried out by using the above-mentioned metal or metal salt as the catalyst, a practical working thereof is economically disadvantageous.

Furthermore, these patent publications disclose only examples directed to the preparation of aromatic isocyanates.

Under this background, development of a process for preparing aliphatic isocyanates having a low reactivity, especially alicyclic isocyanate, economically advantageously is desired.

SUMMARY OF THE INVENTION

It is an object of the present invention to provide a process for the preparation of isocyanates in which a high pressure or gas phase reaction is not used, the equipment cost is not large, the starting materials used are cheap, and by which the intended product is obtained at a high yield, particularly a high space time yield is good.

Another object of the present invention is to provide a high-safety process for the preparation of isocyanate compounds, which comprises obtaining a urethane compound from a diamine and dimethyl carbonate and thermally decomposing the urethane compound.

In accordance with the present invention, there is provided a process for the preparation of an aliphatic diisocyanate compound, which comprises the steps of:

(1) reacting dimethyl carbonate with an aliphatic diamine in the presence of an alkali catalyst to produce a corresponding urethane compound; and, (2) within 48 hours after the completion of the preparation of the urethane compound, thermally decomposing the uretane compound under a reduced pressure of 1 to 700 Torr in a high-boiling-point solvent to produce the aliphatic diisocyanate compound.

DESCRIPTION OF THE PREFERRED EMBODIMENTS

Figure 1:
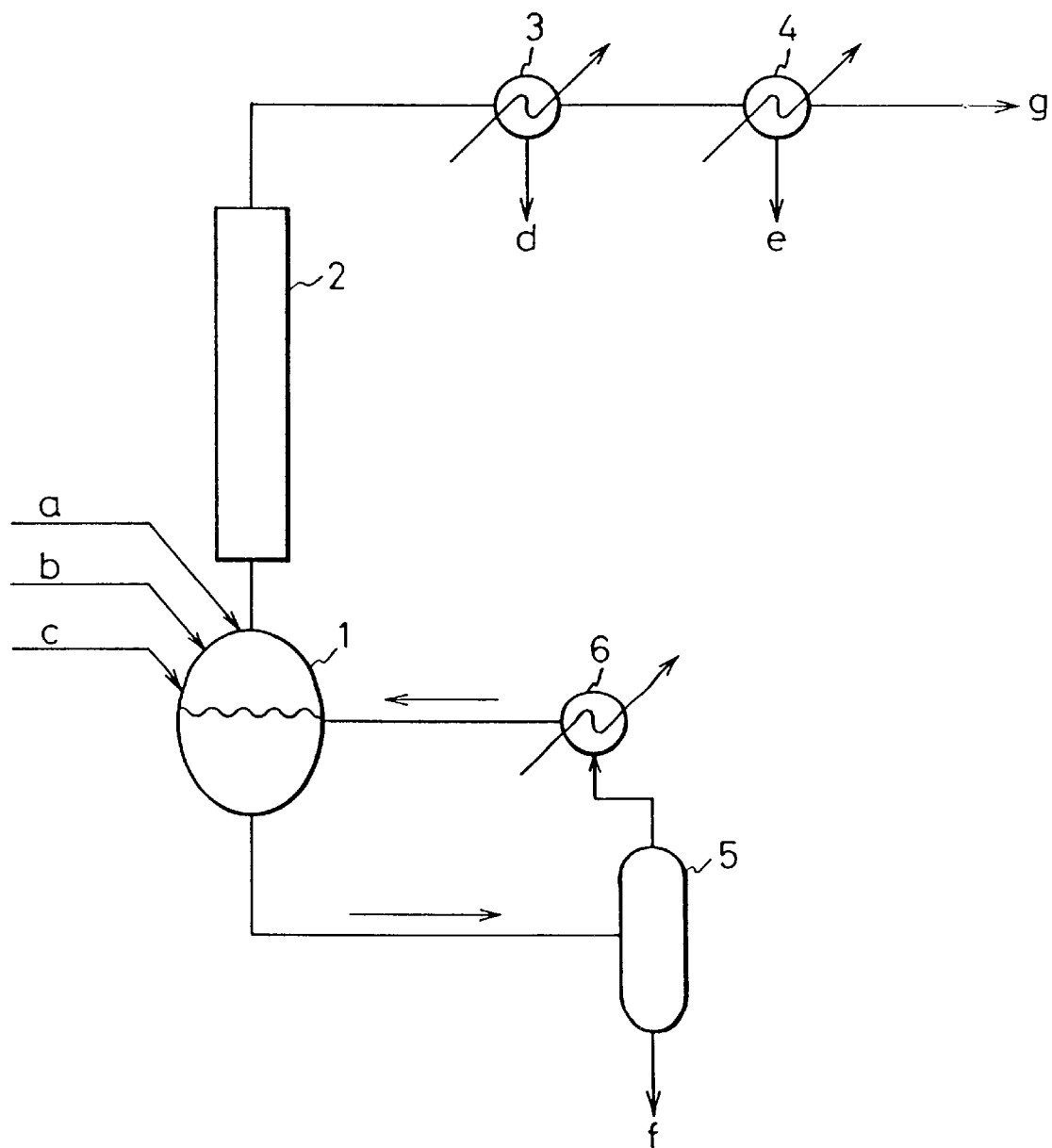
FIG. 1 is a block diagram illustrating the flow whereby the second-stage reaction is continuously carried out.

As pointed out hereinbefore, the first-stage reaction of the present reaction advances according to the following reaction formula:

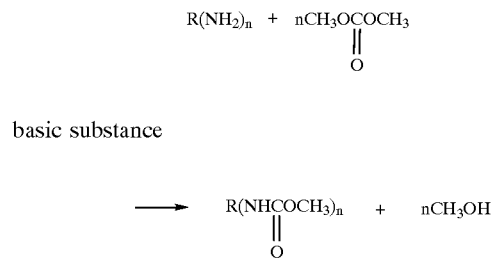

basic substance

A commercially available product of dimethyl carbonate can be used as it is, or after purification if necessary.

Diamines are classified into aromatic diamines and aliphatic diamines by the chemical reactivity. Aliphatic diamines are especially preferably used. The aliphatic diamines are divided into alicyclic diamines having an alicyclic skeleton in the molecule and linear aliphatic diamines having a chain structure. Linear aliphatic amines are preferred but alicyclic diamines are especially suitable. The following diamines can be mentioned as examples of the diamine that can be used in the present invention.

As the alicyclic diamine, there can be mentioned isophorone diamine, 1,4-diaminocyclohexane, 1,3-bis(aminomethyl)cyclohexane, 1,4-bis(aminomethyl)cyclohexane, hydrogenated 4,4-diaminodiphenylmethane and hydrogenated toluylenediamine.

These diamines are valuable because valuable diisocyanates having a cyclic structure can be synthesized therefrom. Especially, the preparation of isophorone diisocyanate, which is a diisocyanate compound having an excellent weatherability, as the intended product from isophorone diamine as the starting material is industrially valuable.

Isophorone diamine includes two isomers, that is, an isomer in which the amino group —$NH_2$ and the aminomethyl group —$CH_2NH_2$ are located at the cis-positions in the cyclohexane ring, and another isomer in which the above groups are located at the trans-positions. Each of these isomers can be used as the starting material in the present invention. A mixture of cis- and trans-isomers, such as commercially available isophorone diamine, can be used without any limitation.

Also, a diamine having amino groups bonded to saturated carbon atoms and an aromatic ring in the skeleton is preferably used as the starting material. As an example of the diamine of this type, there can be mentioned m-xylylenediamine.

As the linear aliphatic diamine, there can be mentioned hexamethylenediamine, 2,2,4-trimethylhexamethylenediamine, 2,4,4-trimethylhexamethylenediamine, tetramethylenediamine and 1,12-diaminododecane.

An aromatic diamine is inferior to an aliphatic diamine in the space time yield or the yield at the urethane formation, but the aromatic diamine can be converted to a urethane according to the present invention.

All of the diamines may contain an ether linkage or a stable group such as a sulfone group, a carbonyl group or a halogen group in the skeleton.

Preferably the water content in the diamine to be used is controlled below 1% by weight before the use thereof. This is because water in the diamine, as well as water in the dimethyl carbonate described hereinafter, reduces the activity of the catalyst.

As the basic substance used as the catalyst at the first-stage reaction in the process for preparing isocyanate compounds according to the present invention, alcoholates of alkali metals and alkaline earth metals are preferred. As the alcoholate, there can be mentioned methylates, ethylates and tertiary butylates of lithium, sodium, potassium, calcium and barium.

Among the basic substances, sodium methylate is especially preferred in view of the availability thereof and for the economical reasons. The amount of sodium methylate used in the present invention is not large enough to cause an economical disadvantage, and a recycling of sodium methylate is not particularly necessary, accordingly, the equipment is simplified. Sodium methylate is commercially available in the form of a methanol solution, which can be easily handled. The basic substance can be used in the form of either a solid or a solution.

A high pressure is not necessary at the first-stage reaction of the preparation process of the present invention, and the reaction is carried out under atmospheric pressure. Nevertheless, the reaction is preferably carried out under such a pressure that will compensate the pressure loss caused by the apparatus structure.

Preferably, the dimethyl carbonate/diamine molar ratio is from 2 to 50 (the dimethyl carbonate/amino group molar ratio is from 1 to 25). More preferably the dimethyl carbonate/diamine molar ratio is at least 4. The reason why the dimethyl carbonate/diamine molar ratio should be controlled to 2 to 50 is that the dimerization reaction is inhibited, and thus, the yield of the urethane compound is improved. If the dimethyl carbonate/diamine molar ratio exceeds 50, the yield of the urethane compound is considerably reduced.

Dimethyl carbonate prepared according to an ordinary process is capable of dissolving a large proportion of water therein, and there is a high risk of a contamination with water. Preferably the water content in dimethyl carbonate used in the present invention is lower than 0.2% by weight. This is because water in dimethyl carbonate reacts with the catalyst to form a metal hydroxide, and the activity of the catalyst is reduced and the amount of the catalyst used must be increased.

The amount of the alkali metal used is determined according to the activity of the catalyst so that the reaction is completed within a reasonably short period of time. For example, sodium methylate is added in an amount such that the content in the crude reaction liquid is 0.001 to 5% by weight, preferably 0.1 to 3% by weight. If the amount of sodium methylate used is smaller than 0.001% by weight, the rate of reaction is low, and if the amount of sodium methylate is larger than 5% by weight, the catalyst is precipitated and the process becomes economically disadvantageous.

The method for carrying out the first-stage reaction is not particularly critical, but in view of a control of the reaction heat, preferably a method is adopted in which the diamine is dropped in dimethyl carbonate.

The reaction temperature can be practically selected in the range of from 0° C. to the boiling point of the crude reaction liquid. But, since the rate of reaction is low at a low temperature and the boiling of methanol formed as a by-product is violent at a high temperature, the reaction temperature is preferably within the range of from 30 to 80° C.

A solvent may be used when the starting material is solid or a prevention of precipitation of the formed urethane compound is desired. For example, solvents inactive to the starting material and product, such as methanol, ethanol, tetrahydrofuran, dioxane, benzene and toluene, can be used.

The kind and amount of the solvent are selected so that the starting material or product having a poor solubility is dissolved under the reaction conditions. If the amount of the solvent used is large and the dilution ratio is high, advance of the reaction is retarded, and the process becomes disadvantageous. Preferably the solvent is used in a minimum amount necessary for the dissolution. In general, preferably the solvent is used in an amount of 1 to 10 times the amount of the formed urethane compound.

When the dimethyl carbonate/diamine molar ratio in the starting materials is close to 2, the concentration of the urethane compound formed in the crude reaction liquid is high. Accordingly, if the crystallizability of the urethane compound is high, to eliminate the risk of precipitation, it is necessary to select a solvent having a high dissolving power. If a solvent having a boiling point lower by at least 10° C. than the boiling point of the formed urethane compound is used, purification by distillation is facilitated and the process becomes economically advantageous.

Especially in the case of the batchwise reaction, a continuous addition of the catalyst or divided intermittent addition of the catalyst in several times with advance of the first-stage reaction is preferable to collective addition of the catalyst, because the amount of the catalyst used can be reduced to ½ to ⅓.

It was found that as shown in the examples given hereinafter, if the catalyst is added continuously or intermittently during the reaction, the necessary amount of the catalyst can be reduced, although the reason therefor is unknown.

If the charging speed of the catalyst for the diamine is high, the boiling of methanol formed as a by-product becomes violent. Accordingly, the charging speed of the catalyst must be controlled, as well as the reaction temperature.

Where the first-stage reaction is carried out in the continuous manner, the catalyst for the diamine can be supplied from not only an inlet in the upstream end portion of a reaction vessel but also an intermediate portion thereof. Furthermore, for example, where the crude reaction liquid is passed through several reactors connected in series, the catalyst can be separately added to the respective reactors.

The formed crude liquid of the urethane compound can be purified to a required purity by an ordinary purification method which includes, for example, consecutive steps of distillation, crystallization, washing with water and then crystallization.

A method in which the alkali component derived from the metal alcoholate as the basic catalyst is neutralized by using an acid such as phosphoric acid and excessive phosphoric acid is the removed by water washing is preferred. If the basic catalyst is heated together with the urethane compound, the urethane compound is further converted to a high-boiling-point compound not intended. Accordingly, this neutralizing step is necessary. The salt formed at the neutralizing step can be removed by an ordinary method such as water washing, filtration or centrifugal separation, and this operation is carried out in combination with the operation of removing methanol. Preferably the formed urethane compound is purified by flash evaporation.

The advantage attained by the use of phosphoric acid at the neutralizing step resides in that, even if the amount of phosphoric acid is too large or too small, the variation of the pH is small and adverse influences are not imposed on the urethane compound at the subsequent purifying step.

Furthermore, preferably a method is adopted in which a crude liquid of the urethane compound is washed with a benzene/water system and the urethane compound is fused and purified by distillation. Benzene is preferred because benzene easily dissolves the urethane compound and the solubility in water is low. The ratio between the amounts used of benzene and water is determined so that the urethane compound is dissolved in benzene at the temperature for the washing treatment of the urethane compound. Generally, benzene is used in an amount of 1 to 10 times the amount of water. Since the solubility differs according to the kind of urethane compound formed, the amount of benzene is appropriately selected within the above-mentioned range according to the kind of urethane compound. Aromatic compounds such as toluene and xylene, and other compounds which are inert and are not soluble in water, such as halogenated hydrocarbons, ether compounds and ester compounds, can be used instead of benzene.

The frequency of washing and the amount of washing liquid are determined so that the amount of water-soluble impurities left in the organic layer is reduced to a predetermined level. The washing can be carried out batchwise or in a continuous manner using an extraction column of the mixer/settler type or the like.

The obtained crude urethane compound can be refined by the flashing method after the neutralization and washing according to the properties of the urethane compound. The degree of this purification has an influence on the yield at the second-stage reaction.

A urethane compound corresponding to the diamine used as the starting material is thus obtained. For example, there can be mentioned 3-methoxycarbonylaminomethyl-3,5,5-trimethyl-1-methoxycarbonylamino -cyclohexane, bis(4-methoxycarbonylaminocyclohexyl)methane, 1,4-bis (methoxycarbonylamino)cyclohexane, 1,4-bis (methoxycarbonylaminomethyl)cyclohexane and 1,3-bis (methoxycarbonylaminomethyl)cyclohexane.

When these compounds are subjected to thermal decomposition as the second-stage reaction, an elimination of alcohols occurs, and isocyanate compounds corresponding to the skeletons of the starting urethanes, such as isophorone diisocyanate, hydrogenated diphenylmethane-4,4-diisocyanate (MDI), cyclohexane diisocyanate and hydrogenated xylylene diisocyanate (XDI) are formed.

The dimethyl carbonate used for the first-stage reaction of the preparation process of the present invention is preferably prepared by a process wherein carbon monooxide and oxygen are reacted with methanol. The thus-prepared dimethyl carbonate is characterized by containing no chlorine and having a high purity, and thus is advantageous over dimethyl carbonate prepared from phosgene.

The thermal decomposition reaction as the second stage reaction will now be described in detail.

At the second stage of the preparation process of the present invention, the urethane compound obtained in the first stage is thermally decomposed under a reduced pressure of 1 to 700 Torr in a high-boiling-point solvent to produce the aliphatic diisocyanate compound.

It is important that the urethane compound obtained in the first stage is subjected to the thermal decomposition without delay, namely, within 48 hours after the completion of the preparation of the urethane compound. More specifically, the period of time from the completion of the preparation of the urethane compound to the initiation of the thermal decomposition of the urethane compound is shorter than 48 hours, preferably shorter than 36 hours, more preferably shorter than 24 hours and most preferably shorter than 16 hours. By the clause "the urethane compound is thermally decomposed within 48 hours after the completion of the preparation of the urethane compoud" herein used, it is meant that, when the urethane compound prepared in the first stage is subjected to a washing step or other purification steps, the thermal decomposition of the urethane compound is initiated within 48 hours after the completion of these washing and other purification steps.

By conducting the thermal decomposition of the urethane compound without delay after the completion of the preparation of the urethane compound, an aliphatic diisocyanate compound can be obtained in a high yield. Furthermore, this procedure is disadvantageous from the following viewpoints. The most urethane compounds prepared in the first step become solid at room temperature and therefore must be maintained at a high temperature until the compounds are subjected to thermal decomposition. When the urethane compounds are maintained in a molten state for a long period of time, the compounds are deteriorated to some extent, the energy consumption is large, a container for storage is needed and the productivity is reduced. It is possible that the molten urethane compounds are partially solidified within 48 hours from the completion of the preparation thereof, but the partially solidified compound can be melted in a short time.

The thermal decomposition of the urethane compound is effected preferably by using a catalyst such as a metal element selected from manganese, molybdenum, tungsten, zinc and beryllium or an inorganic compound or organic compound of said metal, whereby the urethane compound can be converted to a diisocyanate compound in a good yield.

By using the catalyst, a high reaction rate can be attained, and by conducting the reaction under a reduced pressure causing distillation of the formed isocyanate, the isocyanate concentration in the reaction mixture can be maintained at a low level and dimerization or trimerization of the isocyanate group or addition reaction between the isocyanate group and the NH group of the urethane bond, represented by the following formula, can be controlled, and a high yield can be attained:

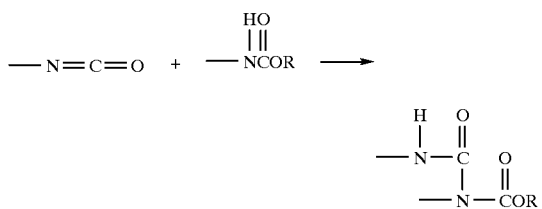

As the compound to be used as the catalyst, there can be mentioned, for example, metallic manganese, manganese oxide (MnO or $Mn_2O_3$), manganese chloride, manganese sulfate, manganese phosphate, manganese borate, manganese carbonate, manganese acetate, manganese naphthenate, manganese (II) acetylacetonate, manganese (III) acetylacetonate, metallic molybdenum, molybdenum trioxide, molybdenum acetylacetonate [$MoO_2(acac)_2$], molybdenum dioxide, metallic tungsten, hexacarbonyl tungsten, tungstic anhydride, tungstric acid, zinc bromide and beryllium acetate. These catalysts can be used in the form of a hydrous salt or an anhydride.

Manganese chloride, manganese sulfate, manganese acetate and manganese naphthenate are especially preferred because they are easily commercially available, are cheap, and have a high activity. Manganese acetate is particularly preferred because a required activity is exerted at a low concentration in the crude reaction liquid.

An optimum amount of the catalyst is determined according to the reactivity of the starting material, the temperature and the kind of the catalyst. If the amount of the catalyst is too small, the rate of reaction is low, and if the amount of the catalyst is too large, the amount of a high-boiling-point by-product tends to increase. In general, most preferably the amount of the catalyst in the solvent is 0.0005 to 5% by weight.

The reaction temperature is preferably 150 to 300° C. If the reaction temperature is lower than 150° C., the formation of the isocyanate is retarded and the process is not practically applicable. At a reaction temperature higher than 300° C., working on an industrial scale is difficult and the process becomes industrially disadvantageous.

The solvent must be inert to the isocyanate compound and the urethane compound, and a solvent selected from aliphatic compounds, aromatic compounds, alkylated aromatic compounds and ether compounds can be used. A compound containing an inactive group such as a halogen group can also be used as the solvent.

A solvent that can be purified and separated from the isocyanate compound is preferred. A solvent having a boiling point considerably different from that of the isocyanate is preferred because purification and separation can be performed by distillation. Since a solvent having a boiling point lower than that of the formed isocyanate compound is distilled together with the isocyanate compound and steps are practically complicated, use of a solvent having a boiling point higher than that of the formed isocyanate is preferred. A solvent having a boiling point higher by at least 10° C. than that of the formed isocyanate compound is especially preferred because the solvent can be easily separated and purified by distillation at the subsequent step.

High-boiling-point by-products are accumulated with the lapse of time, and therefore, a solvent having a boiling point such that regeneration can be industrially performed is preferred.

As preferred examples of the solvent, there can be mentioned o-terphenyl, m-terphenyl, p-terphenyl, a diphenylbenzene mixture, partially hydrogenated triphenyl, dibenzylbenzene, biphenyl, phenyl ether, phenylcyclohexane, hexadecane, tetradecane, octadecane, eicosane, benzyl ether and tetramethylene sulfone.

A suitable solvent must be selected according to the intended isocyanate compound. For example, in the case of the production of isocyanate diisocyanate, partially hydrogenated triphenyl is especially preferred.

The second-stage reaction is carried out under a reduced pressure causing distillation of the formed isocyanate compound from the reaction mixture, whereby the concentration of the isocyanate compound in the reaction mixture is maintained at a low level and a high reaction yield is attained. This effect is especially conspicuous when the reaction is carried out under boiling of the solvent. From this viewpoint, preferably the reaction be carried out under such a reduced pressure that the solvent boils at the adopted reaction temperature. If the degree of reduction of the pressure is too high, recovery of the alcohol formed as the by-product is difficult, and the process becomes disadvantageous in not only the equipment but also the utility. Accordingly, in general, the reaction pressure is at least 1 Torr and lower than 700 Torr, preferably lower than 500 Torr.

The entire amount of the urethane compound, which is the starting material of the second-stage reaction, may be charged in the solvent at the start of the reaction, but in this case, the amount of the solvent used is large and the process becomes disadvantageous. In view of this point, it is preferable to adopt a continuous reaction method in which the urethane compound is continuously charged in the solvent containing the catalyst, which is boiled under a reduced pressure. In the continuous reaction, preferably the solvent containing 0.0005 to 5% by weight of the catalyst is used in an amount 0.2 to 20 times the amount of the urethane to be treated for every hour based on the weight. If the amount of the solvent exceeds the amount 20 times the amount of the urethane compound, the scale of the apparatus must be undesirably large and the process becomes economically disadvantageous.

Supply of the catalyst in the form of a solution in a solvent such as methanol is preferable to supply of the catalyst in the solid or powdery state, because the amount of the catalyst can be decreased. Manganese acetate is preferred as the catalyst because the solubility in methanol is high.

At the second-stage reaction, the yield of the isocyanate compound is remarkably improved by using an assistant such as a triester of phosphorous acid as well as the catalyst. As specific examples of the triester of phosphorous acid used as the assistant, there can be mentioned trialkyl esters of phosphorous acid such as triethyl phosphite and tributyl phosphite, and triaryl esters of phosphorous acid such as triphenyl phosphite and tritolyl phosphite. Among these, a high-boiling-point ester such as triphenyl phosphite is advantageous because volatilization during the reaction is small. Since the formation of the isocyanate is inhibited if the amount of the assistant is too large, it is generally preferred that the molar ratio of the assistant to the urethane compound is lower than $1/100$, especially lower than $1/1000$.

If a reaction apparatus having a structure in which the vapor generated from a reactor is introduced in a distillation column having a reflux device and a fraction rich in the isocyanate compound is obtained in the upper portion of the column is adopted for reducing the amount of the solvent or unreacted starting material incorporated in the formed isocyanate compound, purification of the isocyanate is facilitated and the process becomes advantageous.

Where separation of methanol formed as a by-product from the isocyanate compound is performed, if a first condenser for condensing the isocyanate compound is maintained at a high temperature such that a condensation of methanol does not occur and methanol is condensed in a second condenser maintained at a lower temperature, the isocyanate and methanol can be advantageously separated and recovered. Preferably the first and second condensers are arranged in a vacuum line maintained under a pressure lower than 50 Torr. Where methanol is separated and recovered, absorption in an inert solvent may be adopted instead of condensation in the second condenser.

A high-boiling-point by-product is formed in the solvent with the lapse of time, and this by-product causes addition reaction with the isocyanate group of the isocyanate compound as the product, with the result that the yield of the isocyanate compound is reduced.

As means for preventing this disadvantage, there is adopted a method in which the crude liquid mixture in the reactor is continuously withdrawn and subjected to flash evaporation, a high-boiling-point by-product as the residue in the flash evaporator is removed, an evaporated high-boiling-point solvent-rich gaseous mixture is simultaneously condensed, and a liquid mixture of the condensed solvent, the unreacted urethane compound and the isocyanate compound as the product is returned to the reactor.

In this case, the catalyst is lost while being contained in the withdrawn high-boiling-point by-product, and therefore, the catalyst is additionally charged into the reactor in a corresponding amount. The catalyst withdrawn in the state contained in the high-boiling-point by-product can be recovered and used again. But, since the catalyst used in the process of the present invention is relatively cheap and the amount of the catalyst used is small, the running cost is not greatly increased even if the catalyst is discarded.

The layout of the apparatus in which the above-mentioned second-stage reaction is carried out in a continuous manner is shown in FIG. 1.

Referring to FIG. 1, a distillation column 2 provided with a reflux device is attached to a reactor 1. A first condenser 3 for condensing the isocyanate compound and a second condenser 4 for condensing methanol are attached to the distillation column 2. A catalyst a and a solvent b are placed in the reactor 1, and a urethane compound c is charged under a reduced pressure. A fraction rich in an isocyanate compound d is obtained in the upper portion of the distillation column 2, and the isocyanate compound d is condensed from this fraction in the first condenser 3 and a methanol component e is condensed in the second condenser 4. Symbol q represents a pressure-reducing device. The crude liquid mixture in the reactor 1 is continuously withdrawn and subjected to flash evaporation in a flash evaporator 5, and a high-boiling-point by-product f as the residue is removed and the evaporated high-boiling-point solvent-rich gaseous mixture is condensed in a condenser 6 and returned to the reactor 1.

Figure 2:
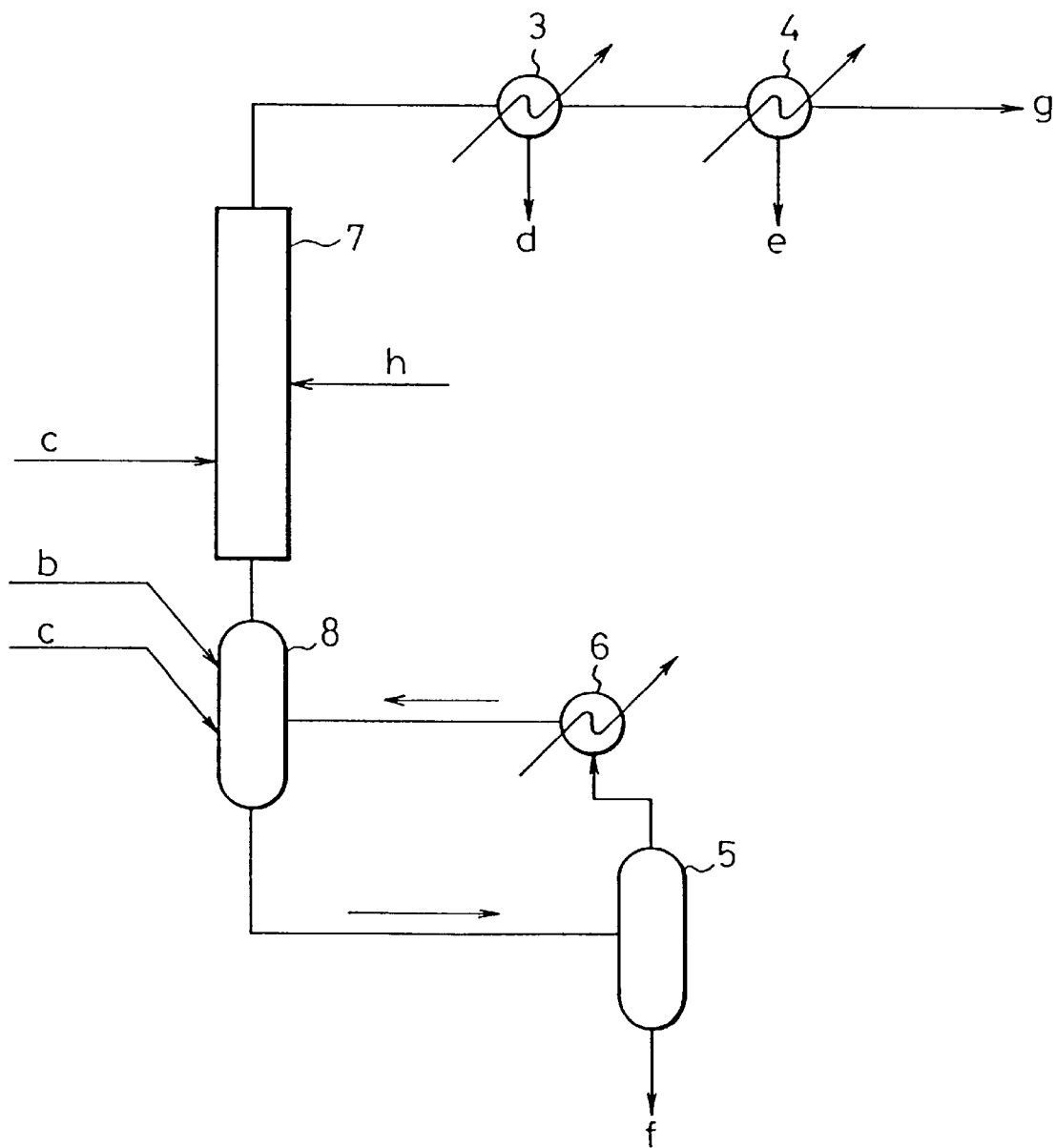
FIG. 2 is another block diagram illustrating the flow whereby the second-stage reaction is continuously carried out.

Preferably, the second-stage reaction of thermally decomposing the urethane compound to obtain a corresponding isocyanate compound is conducted according to a process in which the urethane compound is continuously supplied to the third stage from the bottom of the distillation column or a higher stage and the catalyst is supplied to a stage higher than the stage at which the urethane compound is supplied. If the continuous reaction distillation is carried out while supplying the urethane compound and catalyst to the above-mentioned positions, the intended isocyanate compound can be obtained in a higher yield than the yield attainable when the catalyst, urethane compound and solvent are supplied to the bottom of the distillation column. This process will now be described with reference to FIG. 2.

Reference numeral 8 represents a reboiler, and reference numeral 7 represents a distillation column equipped with a refluxing device. A catalyst/methanol/diisocyanate compound mixed solution h is supplied to this distillation column. The urethane compound c is supplied to a third stage from the bottom or a higher stage, which is lower than the stage where the catalyst-containing mixed solution is supplied. The solvent is supplied to an optional stage or the column bottom.

Reference numeral 3 represents a condenser for condensing and recovering the isocyanate compound, reference numeral 4 represents a condenser for condensing and recovering methanol, reference numeral 5 represents a flash evaporator, and reference numeral 6 represents a condenser for condensing a high-boiling-point solvent-rich mixed gas evaporated at the flash evaporator 5.

The urethane compound as the starting material for the thermal decomposition reaction, the solvent and the catalyst are continuously supplied to the reaction system. The solvent in the reactor is continuously withdrawn together with the high-boiling-point by-product contained in the solvent, and simultaneously, the solvent free of the high-boiling-point product is supplied to the reactor. Since the catalyst is withdrawn together with the thus withdrawn solvent, the catalyst is continuously charged in an amount corresponding to the lost amount to maintain the catalyst concentration at a constant value. A method can be adopted in which the urethane compound is premixed with the solvent and the mixture is charged into the reaction system.

When manganese acetate is used as the catalyst, the catalyst is generally supplied in the form of a methanol solution, but since the temperature in the reaction system is higher than the boiling point of methanol and the catalyst tends to precipitate, the boiling point of the methanol solution is elevated by further adding the diisocyanate, which is the intended product, to the methanol solution. Namely, the catalyst is dissolved in methanol and the diisocyanate is then added to the solution to form a diisocyanate solution of the catalyst.

The mix ratio of the catalyst and methanol is adjusted so that a homogeneous solution having a low viscosity can be obtained. If the amount of methanol is too large, the necessary amount of the diisocyanate compound to be then added must be increased, and thus the process becomes economically disadvantageous. Preferably, methanol is used in an amount 0.2 to 1,000 times the amount of the catalyst, based on the weight.

The mix ratio of the methanol solution and the diisocyanate compound is adjusted so that the formed mixed solution has a low viscosity and the catalyst is not precipitated by the mixing.

At this point, care should be taken that a reaction of methanol with the diisocyanate compound, to convert the diisocyanate compound to the original urethane compound, does not occur.

In general, a compound having an isocyanate group has higher melting point and viscosity than those of a corresponding compound having a urethane group. Accordingly, preferably the mixing ratio is selected so that, even if all of the isocyanate compound and methanol are reacted, the viscosity is not elevated. From this viewpoint, most preferably more diisocyanate is contained than methanol, because the viscosity of the solution is thus kept low. Nevertheless, even if the amount of diisocyanate is almost equivalent to the amount of methanol, precipitation does not occur when the tank or supply line is appropriately heated or the urethane compound per se has a low viscosity.

Furthermore, even more methanol is contained than diisocyanate, the viscosity is kept low by the diluting effect of the methanol, and thus the process can be carried out. Nevertheless, since the gasification of ethanol is violent at the time of charging, heating or the like is sometimes necessary.

The reason why the catalyst insoluble in the diisocyanate gives a homogeneous solution when the catalyst is first dissolved in methanol and the solution is then mixed with the diisocyanate has not been elucidated, but it is assumed that, since the formed urethane bond has a polarity, a coordination of the catalyst with this urethane bond will result in the solubilization of the catalyst.

Preferably, the diisocyanate is used in an amount 0.001 to 1,000 times the amount of the methanol solution based on the weight. If the amount of the diisocyanate is too small and outside this range, there is a risk of precipitation of the catalyst at the time of charging into the reactor. If the amount of the diisocyanate is too large and outside this range, the vapor load on the column is increased, resulting in an economical disadvantage. Most preferably, the amount of the diisocyanate is 1 to 1,000 times the amount of the methanol solution based on the weight.

Methanol is preferably used because it is a substance formed by decomposition, and a complicated purification system is not necessary. The diisocyanate used need not be a pure product, and a crude product containing the monoisocyanate or solvent can be used.

If the urethane compound and catalyst are charged in the distillation column in the above-mentioned manner, since the urethane compound and catalyst flow downward in the column, the decomposition of the urethane bond of the monoisocyanate in the column is promoted, resulting in an increase of the conversion during the decomposition reaction, and the decomposition reaction occurring at the column bottom, which is a high-temperature zone, is controlled and the high-boiler reaction by the isocyanate group or urethane group is controlled. Namely, when a comparison based on the same reaction apparatus is made, a higher reaction conversion is obtained while controlling the high-boiler reaction, the purity of the formed diisocyanate is increased, and the space-time yield is improved.

The number of stages of the distillation column used is not particularly critical, and the stage number is appropriately selected according to the kinds of the urethane compound to be decomposed, the diisocyanate to be formed, and the solvent used. Preferably, a distillation column having 1 to 100 stages is used.

The urethane compound is supplied to the third stage, or a higher stage, from the bottom of the distillation column, at which the temperature and residence time are sufficient to complete the decomposition reaction.

The stage at which the catalyst solution is supplied is not particularly critical, so long as the stage is higher than the stage at which the urethane compound is supplied. Since the portion below the position of charging of the catalyst solution constitutes a reaction zone, if the charge position of the catalyst solution is too low, the decomposition of the monoisocyanate is insufficient and good results cannot be obtained. If the charge position of the catalyst solution is too high, the monoisocyanate in the catalyst solution is distilled and the process becomes disadvantageous. Accordingly, an optimal position is selected according to the kind of the diisocyanate to be produced.

The methanol and diisocyanate compound in the catalyst/methanol/diisocyanate compound mixed solution supplied into the distillation column are mixed with the diisocyanate compound formed by the decomposition reaction and distilled at the head of the distillation column 7, and the diisocyanate compound and methanol are separated by the condensers 3 and 4, respectively.

On the other hand, the high-boiling-point product containing the catalyst flows downward from the distillation column 7 and drops into the reboiler 8. Namely, the diisocyanate compound used in the present invention is a part of the product, which is always circulated.

To reduce the amounts of the solvent and unreacted starting material incorporated into the diisocyanate compound as the intended product, and facilitate the purification of the diisocyanate compound, there is preferably adopted a reaction apparatus having a structure such that the vapor generated from the reactor is introduced into a distillation column equipped with a refluxing device and a diisocyanate compound-rich fraction is obtained in the upper portion of the column.

For the separation of methanol formed as the by-product from the diisocyanate compound, the condenser 3 for separating and recovering the diisocyanate compound is maintained at a high temperature at which condensation of methanol will not occur, and methanol is condensed at the second condenser 4 maintained at a lower temperature. According to this method, the diisocyanate is advantageously separated from methanol and recovered.

Instead of the method using the second condenser 4 for separation and recovery of methanol, a method can be adopted in which methanol is absorbed in an inert solvent.

If the high-boiling-point by-product formed is accumulated in the solvent with the lapse of time, this by-product causes an addition reaction with the diisocyanate compound as the intended product, with the result that the yield of the diisocyanate compound is reduced. To control the formation and accumulation of the high-boiling-point by-product, preferably a method is adopted in which the crude product liquid mixture in the reactor is continuously withdrawn and flash-evaporated, the high-boiling-point by-product as the residue in the flash evaporator is removed, the evaporated high-boiling-point solvent-rich gaseous mixture is simultaneously condensed, and the liquid mixture of the condensed solvent, the unreacted urethane compound and the diisocyanate compound as the product is returned to the reactor. The high-boiling-point by-product also can be removed by using a distillation column instead of the flash evaporator, but in this case, the catalyst is lost while being carried by the withdrawn high-boiling-point by-product, and accordingly, the catalyst must be additionally charged into the reaction system in an amount corresponding to the amount lost.

The separation of the reaction product obtained by the second-stage reaction of the thermal decomposition will now be described.

In general, the monoisocyanate compound formed as the by-product is contained in the diisocyanate compound as the intended product. The amount of the monoisocyanate compound incorporated depends on the reaction temperature, the kind of starting urethane compound, the kind of corresponding diisocyanate compound formed, the kind of monoisocyanate compound formed, the boiling point of the solvent used, the stage number of the used distillation column, the reflux ratio, the running temperature and pressure, and the like. In general, however, the amount of the monoisocyanate compound incorporated is in the order of several % to scores of %.

Among the compounds contained in the reaction mixture, the intended diisocyanate compound has a lowest molecular weight, and thus, the boiling point thereof is low. Accordingly, if the decomposition reaction is carried out in the distillation column, the intended diisocyanate compound is obtained from the column head.

The purity of the diisocyanate compound obtained from the reaction system can be increased, for example, by increasing the reaction conversion or by elevating the reaction temperature, but a high-temperature heating medium is necessary for this purpose, and thus the energy costs are increased.

The distillation process is generally adopted for obtaining the diisocyanate compound, which is an industrially effective component, from the above-mentioned mixture while removing the monoisocyanate compound from the mixture.

Isocyanate compounds are thermally unstable, however, and therefore, if a separation by mere distillation is intended, a polymerization occurs in the reboiler of the distillation column and the yield is reduced. Moreover, the formed polymer blocks the reboiler, rendering operation impossible.

This problem can be solved by the process in which, when the crude reaction liquid formed by the thermal decomposition, which comprises the monoisocyanate compound and diisocyanate compound as the main components, is separated in the respective components, a high-boilingpoint heating medium is supplied to the bottom or an optional stage of the distillation column and the separation is effected by distillation.

Figure 3:
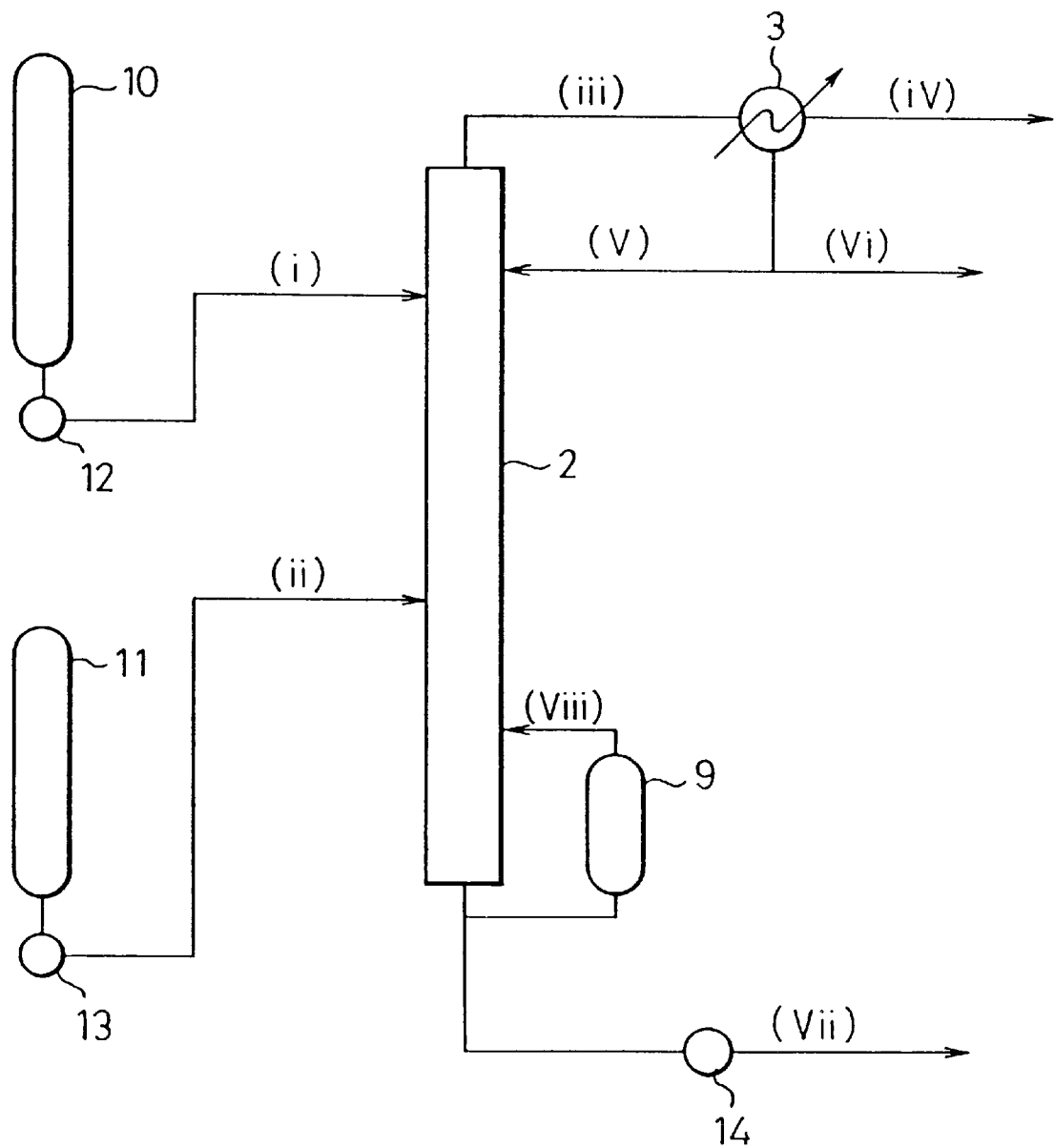
FIG. 3 is a block diagram illustrating the flow whereby the second-stage reaction product is separated.

This distillation separation process will now be described with reference to FIG. 3. In FIG. 3, reference numeral 2 represents a distillation column, reference numeral 3 represents a condenser for collecting an isocyanate compound, reference numeral 9 represents a reboiler, reference numeral 10 represents a tank for storing an isocyanate compound therein, reference numeral 11 represents a tank for storing a high-boiling-point heating medium therein, reference numerals 12 and 13 represent pumps for charging an isocyanate compound and a high-boiling-point heating medium, respectively, and reference numeral 14 represents a pump for withdrawal from the reboiler. Arrows indicate the flow directions of substances at the respective points. Furthermore, marks (i) through (viii) indicate liquids flowing at the respective parts.

For example, when isophorone diisocyanate is synthesized from isophoronediamine and dimethyl carbonate through isophorone dicarbamate, the main liquids flowing at parts (i) through (vii) and approximate contents (% by weight) thereof are as follows.

Part (i)

Isophorone diisocyanate (IPDI): 95 to 99%

Isophorone monoisocyanate (IPMI): 1 to 5%

Part (ii)

High-boiling-point heating medium: about 90%

Others: about 10%

Parts (iii) and (iv)

Methanol alone

Parts (v) and (vi)

IPDI: 99.5 to 100%

IPMI: 0 to 0.5%

Methanol: trace

Part (vii)

High-boiling-point heating medium: 90 to 99%

Others: 1 to 10%

The liquid mixture comprising the monoisocyanate compound and diisocyanate compound as the main components is the liquid corresponding to the reaction product liquid formed by the second-stage reaction of the thermal decomposition, and the mixture of this liquid (i) and the liquid (ii) is supplied to the distillation column 2. The stage to which the liquid mixture is supplied is appropriately selected according to the amount of the monoisocyanate compound contained in the diisocyanate compound. The high-boiling-point heating medium is continuously supplied to the bottom or an optional stage, of the distillation column.

The diisocyanate compound coming in the form of a vapor from the distillation column 2 is condensed by the condenser 3 and is recovered as the product. The monoisocyanate compound and the high-boiling-point heating medium are continuously withdrawn from the bottom of the distillation column 2, and the withdrawn monoisocyanate compound and high-boiling-point heating medium are continuously supplied to the distillation column for thermally decomposing the urethane compound.

By adopting this process, the monoisocyanate compound and diisocyanate compound can be recovered at a high efficiency. The operation temperature can be appropriately determined according to the physical properties of the isocyanate compounds.

The high-boiling-point heating medium used must be inactive to the isocyanate compounds, and a heating medium selected from aliphatic compounds, aromatic compounds, alkyl compounds and ether compounds is used. These compounds may contain an inactive group such as a halogen substituent. Use of a high-boiling-point heating medium that can be easily separated from the intended diisocyanate compound by purification is preferable. For example, a heating medium having a boiling point far different from that of the diisocyanate compound is preferably used, because the purification and separation can be thus performed by distillation. When a heating medium having a boiling point lower than that of the diisocyanate compound is used, the heating medium is distilled together with the diisocyanate compound and the process becomes disadvantageously complicated. Accordingly, a heating medium having a boiling point higher than that of the diisocyanate compound is preferably used. A heating medium having a boiling point higher by at least 10° C. than that of the diisocyanate compound is more preferable because the heating medium is easily separated from the diisocyanate compound by distillation.

As preferable heating media, there can be mentioned o-terphenyl, m-terphenyl, p-terphenyl, mixed diphenylbenzenes, partially hydrogenated triphenyl, dibenzylbenzene, biphenyl, phenyl ether, phenylcyclohexane, hexadecane, tetradecane, octadecane, eicosane, benzyl ether, tetramethyl ether and dibenzyltoluene.

An appropriate heating medium should be selected according to the kind of the intended diisocyanate compound. For example, m-terphenyl or dibenzyltoluene is especially preferably used for the production of isophorone diisocyanate.

A method can be adopted a method in which the isocyanate compounds are premixed with the heating medium and the mixture is supplied to the distillation column.

The ratio of the high-boiling-point heating medium used to the diisocyanate compound is optionally selected from the range of from 1/10 to 10/1. If the mixing ratio of the high-boiling-point heating medium is too high, the equipment efficiency and thermal efficiency are low, and if the mixing ratio of the high-boiling-point heating medium is too low, the effect is unsatisfactory.

The present invention will now be described in detail with reference to the following examples.

EXAMPLE 1

Stage One

A round-bottom flask provided with a stirrer was charged with 158.7 g of dimethyl carbonate which was prepared by reacting carbon monoxide and oxygen with methanol, and the content was heated to 70° C. under a nitrogen gas atmosphere with stirring. Into the flask, 3.97 g of a solution of sodium methylate in a 28 % methanol solution and 75 g of isophorone diamine (IPDA) were charged at a uniform charging rate by using two charging pumps over a period of 120 minutes while the mixture was maintained at 70° C.. After termination of the charging, the reaction mixture was aged at 70° C. for 3 hours, cooled to 40° C. and then neutralized with phosphoric acid.

The thus-prepared crude reaction solution was analyzed by gas chromatography and it was confirmed that a urethane compound corresponding to IPDA, that is, 3-methoxycarbonylaminomethyl-3,5,5-trimethyl-1-methoxycarbonylaminocyclohexane, was produced in a yield of 98.1% based on IPDA.

The crude reaction solution was further aged for 3 hours (i.e, the total aging time was 6 hours) and it was confirmed that isophorone dicarbamate (IPDC) was produced in a yield of 99.5% based on IPDA.

The crude reaction solution was subjected to a low-boiling point ingredient-removing treatment at 150° C. and water was then added in an amount of 1.25 times the amount of the crude reaction solution while the temperature was maintained at 95° C., whereby the crude reaction product was washed with water.

Stage Two

The thus-prepared isophorone dicarbamate (IPDC) was allowed to stand for 8 hours at 130° C. Then, using a glass reboiler having a capacity of 300 ml, to which a ten-staged Oldar-Show column was set, and further using dibenzyltoluene as a solvent, the continuous decomposition of the thus-prepared isophorone dicarbamate was carried out as follows.

The reboiler was charged with 117 ml of dibenzyltoluene and 10 ppm, based on dibenzyltoluene, of anhydrous manganese acetate and the mixture was heated under a reduced pressure of 10 Torr until boiling occurred. Then, a liquid mixture composed of 59.0% by weight of IPDC and 41.0% by weight of dibenzyltoluene was charged in the reboiler at a rate of 120 g/hr. Isophorone diisocyanate (IPDI) was withdrawn as the product from the top of the distillation column. The operation was carried out while withdrawing the liquid at a rate such that the liquid in the reactor was kept at a constant level.

Warm water maintained at 60° C. was passed through a condenser to condense the IPDC component, and methanol was allowed to escape as gas. During the operation, a methanol solution containing 125 ppm of anhydrous manganese acetate was added to the reaction liquid in an amount corresponding to the amount of the withdrawn liquid so that the concentration of anhydrous manganese acetate in the reactor was maintained at 10 ppm.

When the temperature in the column, the amount of the distillate, the amount of the withdrawn liquid and the composition became substantially constant, distillate was produced at a rate of 52.6 g per hour and was composed of 77.3% by weight of IPDI, 22.7% by weight of monoisocyanate (IPMI) and 0.05% by weight of dibenzyltoluene. The temperature of the reaction mixture was 245° C.

The conversion of IPDC was 99% by weight and the high boiler reaction ratio of IPDC was 6% by weight. The yields of IPDI and IPMI were 74% and 19%, respectively, based on the charged IPDC.

EXAMPLES 2 THROUGH 4 AND COMPARATIVE EXAMPLE 1

Following the same procedures employed in Example 1, synthesis of isophorone dicarbamate (IPDC) and thermal decomposition of IPDC were carried out wherein the standing time of isophorone dicarbamate (IPDC) after the preparation thereof and before the thermal decomposition thereof was changed as shown in Table 1. All other conditions remained substantially the same. The results are shown in Table 1.

TABLE 1

| Example No. | Standing time *1 (hrs) | Conversion of IPDC (%) | High-boiler reaction ratio (%)*2 | Yield of IPDI *3 (%) | Yield of IPMI *4 (%) |
| --- | --- | --- | --- | --- | --- |
| Example 1 | 8 | 99 | 6 | 74 | 19 |
| Example 2 | 16 | 99 | 11 | 71 | 18 |
| Example 3 | 20 | 99 | 13 | 69 | 17 |
| Example 4 | 25 | 99 | 16 | 67 | 17 |

TABLE 1-continued

| Example No. | Standing time *1 (hrs) | Conversion of IPDC (%) | High-boiler reaction ratio (%)*2 | Yield of IPDI *3 (%) | Yield of IPMI *4 (%) |
| --- | --- | --- | --- | --- | --- |
| Comparative Example 1 | 48 | 99 | 26 | 58 | 15 |

*1 Standing time spanning from the completion of preparation and purification of isophorone dicarbamate (IPDC) to the initiation of thermal decomposition of IPDC (hours)
*2High-boiler reaction ratio of IPDC (%)
*3 Yield of isophorone diisocyanate (IPDI) based on the charged IPDC (%)
*4 Yield of isophorone monoisocyanate (IPMI) based on the charged IPDC (%)

We claim:

1. A process for the preparation of an aliphatic diisocyanate compound or a diisocyanate compound which has an aromatic ring and in which the nitrogen atoms of the isocyanate groups are bonded to the saturated carbon atom, which consists of a single synthetic process free of any delay or interruptions and comprises a two-stage reaction consisting of the steps of:
   (1) reacting dimethyl carbonate with an aliphatic diamine or a diamine having amino groups bonded to saturated carbon atoms and having an aromatic ring in the skeleton in the presence of an alkali catalyst to produce a corresponding urethane compound; and
   (2) within 48 hours of carrying out step (1) and after the completion of the preparation of the urethane compound, thermally decomposing the urethane compound under a reduced pressure of 1 to 700 Torr in a high-boiling-point solvent to produce the aliphatic diisocyanate compound or a diisocyanate compound which has can aromatic ring and in which the nitrogen atoms of the isocyanate groups are bonded to the saturated carbon atom.

2. A process for the preparation of a diisocyanate compound according to claim 1, wherein the dimethyl carbonate used in the step (1) is prepared by reacting carbon monoxide and oxygen with methanol.

3. A process for the preparation of a diisocyanate compound according to claim 1, wherein the dimethyl carbonate is reacted with a diamine having amino groups bonded to saturated carbon atoms and having an aromatic ring in the skeleton of the diamine.

4. A process for the preparation of a diisocyanate compound according to claim 3, wherein the diamine is isophorone diamine.

5. A process for the preparation of a diisocyanate compound according to claim 1, wherein the thermal decomposition of the urethane compound is initiated within 36 hours after the completion of the preparation of the urethane compound.

6. A process for the preparation of a diisocyanate compound according to claim 1, wherein the thermal decomposition of the urethane compound is initiated within 24 hours after the completion of the preparation of the urethane compound.

7. A process for the preparation of a diisocyanate compound according to claim 1, wherein the thermal decomposition of the urethane compound is initiated within 16 hours after the completion of the preparation of the urethane compound.

8. A process for the preparation of a diisocyanate compound according to claim 1, wherein the thermal decomposition of the urethane compound is carried out in the presence of a catalyst comprised of at least one metal element selected from the group consisting of manganese, molybdenum, tungsten, zinc and beryllium or a compound of said metal, or at least one member selected from the group consisting of tetrabutyl titanate, dibutyltin laurate, tin octylate, iron halides, potassium borate, cerium (III) sulfate, dipotassium hydrogen phosphate, brass, and tin (IV) chloride.

9. A process for the preparation of a diisocyanate compound according to claim 1, wherein the alkali catalyst used in the step (1) is sodium methylate.

10. A process for the preparation of a diisocyanate compound according to claim 9, wherein sodium methylate used as the catalyst is continuously or intermittently added.

11. A process for the preparation of a diisocyanate compound according to claim 1, wherein the ratio of the dimethyl carbonate charged to the diamine charged in the step (1) is from 2 to 50 by mole.

12. A process for the preparation of a diisocyanate compound according to claim 1, wherein the content of water in the dimethyl carbonate used in the step (1) is controlled to below 0.2% by weight.

13. A process for the preparation of a diisocyanate compound according to claim 1, wherein a crude liquid of the urethane compound as the product of the step (1) is neutralized with phosphoric acid.

14. A process for the preparation of a diisocyanate compound according to claim 13, wherein the neutralized liquid is washed with water.

15. A process for the preparation of a diisocyanate compound according to claim 13, wherein the neutralized liquid is subjected to flash distillation.

16. A process for the preparation of a diisocyanate compound according to claim 1, wherein the content of water in the diamine used in the step (1) is controlled below 1% by weight.

17. A process for the preparation of a diisocyanate compound according to claim 1, wherein a crude liquid of the urethane compound as the product at the step (1) is washed with a benzene/water mixture.

18. A process for the preparation of a diiscyanate compound according to claim 17, wherein the washed urethane compound is fused and subjected to purification by distillation.

19. A process for the preparation of a diisocyanate compound according to claim 1, wherein methanol produced at the thermal decomposition step (2) is removed through a vacuum line maintained at a pressure lower than 50 Torr.

20. A process for the preparation of a diisocyanate compound according to claim 1, the high-boiling-point solvent used in the step (2) is partially hydrogenated triphenyl.

21. A process for the preparation of a diisocyanate compound according to claim 8, wherein the catalyst used in the step (2) is at least one member selected from the group consisting of manganese, molybdenum, tungsten, zinc and beryllium, and compounds of these metals.

22. A process for the preparation of a diisocyanate compound according to claim 8, wherein the catalyst used in the step (2) is tetrabutyl titanate, dibutyl laurate or tin octylate.

23. A process for the preparation of a diisocyanate compound according to claim 8, wherein the iron halide is iron (III) chloride or iron (II) bromide.

24. A process for the preparation of a diisocyanate compound according to claim 8, wherein the catalyst used in the step (2) is manganese acetate.

25. A process for the preparation of a diisocyanate compound according to claim 8, wherein the catalyst used in the step (2) is at least one member selected from the group consisting of manganese sulfate, manganese chloride and manganese naphthenate.

26. A process for the preparation of a diisocyanate compound according to claim 8, wherein the catlyst used in the step (2) is zinc bromide.

27. A process for the preparation of a diisocyanate compound according to claim 8, wherein the catalyst used in the step (2) is continuously added in the form of a solution in methanol.

28. A process for the preparation of a diisocyanate compound according to claim 1, wherein the thermal decomposition in the step (2) is carried out in a multi-stage distillation column, in which the urethane compound is continuously supplied to the third stage or a higher stage, from the bottom of the distillation column and the catalyst is supplied to a stage higher than the stage at which the urethane compound is supplied.

29. A process for the preparation of a diisocyanate compound according to claim 1, wherein the catalyst is supplied as a mixture thereof with methanol and a diisocyanate compound.

30. A process for the preparation of a diisocyanate compound according to claim 1, wherein the thermal decomposition in the step (2) is carried out in the presence of a triester of phosphorous acid.

31. A process for the preparation of a diisocyanate compound according to claim 30, wherein the triester of phosphorous acid is triphenyl phosphite.

32. A process for the preparation of a diisocyanate compound according to claim 30, wherein the amount of the triester of phosphorous acid is such that the molar ratio of the triester of phosphorous acid to the urethane compound is from $1/1,000$ to $1/100$.

33. A process for the preparation of a diisocyanate compound according to claim 1, wherein a crude reaction liquid produced by the thermal decomposition in the step (2), which comprises an aliphatic monoisocyanate compound and an aliphatic diisocyanate compound as the main components, is separated into these two compounds by distillation, while a high-boiling-point heating medium is supplied to the bottom or an optional stage of a distillation column.

34. A process for the preparation of a diisocynate compound according to claim 33, wherein the high-boiling-point heating medium has a boiling point of at least 10° C. higher than that of the diisocyanate compound, and is selected from the group consisting of o-terphenyl, m-terphenyl, p-terphenyl, mixed diphenylbenzenes, partially hydrogenated triphenyl, dibenzylbenzene, biphenyl, phenyl ether, phenylcyclohexane, hexadecane, tetradecane, octadecane, eicosane, benzyl ether, tetramethyl ether and dibenzyltoluene.

* * * * *

UNITED STATES PATENT AND TRADEMARK OFFICE
CERTIFICATE OF CORRECTION

PATENT NO.   : 5,914,428
DATED        : June 22, 1999
INVENTOR(S)  : Toyokazu Yagii, et al.

It is certified that error appears in the above-identified patent and that said Letters Patent is hereby corrected as shown below:

Item [30] Foreign Application Priority Data
| Date | Country | Number |
|---|---|---|
| Jan. 13, 1987 | [JP] Japan | 62-4085 |
| Jun. 18, 1987 | [JP] Japan | 62-152032 |
| Nov. 11, 1987 | [JP] Japan | 62-284442 |
| Dec. 16, 1987 | [JP] Japan | 62-316180 |
| Jan. 13, 1988 | [WO] WIPO | PCT/JP88/00026 |
| Jan. 13, 1989 | [JP] Japan | 1-7252 |
| Jun. 1, 1989 | [JP] Japan | 1-139505 |

Signed and Sealed this

Ninth Day of October, 2001

Attest:

NICHOLAS P. GODICI
Attesting Officer    Acting Director of the United States Patent and Trademark Office